(12) United States Patent
Wang et al.

(10) Patent No.: US 9,328,043 B2
(45) Date of Patent: May 3, 2016

(54) PROCESS FOR PRODUCING 2,3,3,3-TETRAFLUOROPROPENE

(71) Applicant: HONEYWELL INTERNATIONAL INC., Morristown, NJ (US)

(72) Inventors: Haiyou Wang, Amherst, NY (US); Selma Bektesevic, Williamsville, NY (US); Hsueh S. Tung, Getzville, NY (US); Haluk Kopkalli, Staten Island, NY (US); Yuon Chiu, Denville, NJ (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

(21) Appl. No.: 14/382,082

(22) PCT Filed: Feb. 25, 2013

(86) PCT No.: PCT/US2013/027606
§ 371 (c)(1),
(2) Date: Aug. 29, 2014

(87) PCT Pub. No.: WO2013/130385
PCT Pub. Date: Sep. 6, 2013

(65) Prior Publication Data
US 2015/0011804 A1  Jan. 8, 2015

Related U.S. Application Data

(60) Provisional application No. 61/604,629, filed on Feb. 29, 2012.

(51) Int. Cl.
| | | |
|---|---|---|
| C07C 17/35 | (2006.01) | |
| C07C 17/20 | (2006.01) | |
| C07C 17/38 | (2006.01) | |

(52) U.S. Cl.
CPC ............... *C07C 17/35* (2013.01); *C07C 17/206* (2013.01); *C07C 17/38* (2013.01)

(58) Field of Classification Search
CPC ........ C07C 17/35; C07C 17/38; C07C 17/206
USPC ......................................................... 570/153
See application file for complete search history.

(56) References Cited

U.S. PATENT DOCUMENTS

| | | |
|---|---|---|
| 2,931,840 A | 4/1960 | Marquis |
| 4,900,874 A | 2/1990 | Ihara et al. |
| 5,162,594 A | 11/1992 | Krespan |
| 7,795,480 B2 | 9/2010 | Merkel et al. |
| 8,058,486 B2 | 11/2011 | Merkel et al. |
| 2007/0197842 A1 | 8/2007 | Mukhopadhyay et al. |
| 2009/0099296 A1 | 4/2009 | Kamikawa |
| 2009/0240090 A1 | 9/2009 | Merkel et al. |
| 2011/0087055 A1 | 4/2011 | Tirtowidjojo et al. |
| 2011/0105807 A1 | 5/2011 | Kopkalli et al. |
| 2011/0130599 A1 | 6/2011 | Elsheikh et al. |
| 2011/0155942 A1 | 6/2011 | Pigamo et al. |
| 2011/0201853 A1 | 8/2011 | Tung et al. |
| 2012/0010449 A1 | 1/2012 | Wismer et al. |

FOREIGN PATENT DOCUMENTS

| | | |
|---|---|---|
| CN | 1976885 A | 6/2007 |
| CN | 102001910 A | 4/2011 |
| WO | WO2009015317 A1 | 1/2009 |
| WO | 2010111067 A1 | 9/2010 |
| WO | WO 2010/123154 A2 | 10/2010 |
| WO | WO 2011/087825 A1 | 7/2011 |
| WO | WO 2011/110889 A1 | 9/2011 |

OTHER PUBLICATIONS

International Search Report dated Jun. 21, 2013 issued in PCT/US2013/027606.
Banks, R.E. et al., Preparation of 2,3,3,3-tetrafluoropropene from trifluoroacetylacetone and sulphur tetrafluoride, Journal of Fluorine Chemistry, (1997) vol. 82, pp. 171-174.
Chinese Office Action dated Apr. 7, 2015 corresponding to Chinese Patent Appln. No. 201380011736.2.
European Search Report dated Jan. 10, 2015 corresponding to European Patent Appln. No. 13754533.1.

*Primary Examiner* — Shailendra Kumar
(74) *Attorney, Agent, or Firm* — Scully, Scott, Murphy & Presser

(57) ABSTRACT

The present invention relates, in part, an improved process for the production of certain hydrofluoroolefins, particularly 2,3,3,3-tetrafluoropropene (1234yf). In certain non-limiting embodiments, the invention relates to methods for improving process efficiency during the fluorination of 1,1,2,3-tetrachloropropene, 2,3,3,3-tetrachloropropene, and/or 1,1,1,2,3-pentachloropropane to 2-chloro-3,3,3-trifluoropropene by separating and recycling unreacted HF, unreacted starting materials, and/or certain process intermediates from the 2-chloro-3,3,3-trifluoropropene product stream.

25 Claims, 2 Drawing Sheets

PROCESS FOR PRODUCING 2,3,3,3-TETRAFLUOROPROPENE

CROSS REFERENCE TO RELATED APPLICATIONS

This application is a '371 of PCT Application No. PCT/US2013/027606 filed Feb. 25, 2013 which claims the benefit of U.S. Provisional Application No. 61/604,629, filed Feb. 29, 2012, the entire contents of both of which are incorporated herein by reference.

FIELD OF THE INVENTION

The present invention relates to a process for preparing fluorinated organic compounds, more particularly to a process for preparing fluorinated olefins, and even more particularly to a process for producing 2,3,3,3-tetrafluoropropene (HFO-1234yf).

BACKGROUND OF THE INVENTION

Certain hydrofluoroolefins (HFOs), such as tetrafluoropropenes (including 2,3,3,3-tetrafluoropropene (HFO-1234yf)), are now known to be effective refrigerants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike most chlorofluorocarbons (CFCs) and hydrochlorofluorocarbons (HCFCs), most HFOs pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf is a leader among the materials being developed for use in many of the aforementioned applications.

Several methods of preparing HFOs are known. For example, U.S. Pat. No. 4,900,874 (Ihara et al) describes a method of making fluorine containing olefins by contacting hydrogen gas with fluorinated alcohols. Although this appears to be a relatively high-yield process, commercial scale handling of hydrogen gas at high temperature is potentially hazardous. Also, the cost of commercially producing hydrogen gas, such as building an on-site hydrogen plant, is economically costly.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted to unwanted and/or unimportant byproducts, including a sizeable amount of carbon black which tends to deactivate the catalyst used in the process.

The preparation of HFO-1234yf from trifluoroacetylacetone and sulfur tetrafluoride has been described (See Banks, et al., Journal of Fluorine Chemistry, Vol. 82, Iss. 2, p. 171-174 (1997)). Also, U.S. Pat. No. 5,162,594 (Krespan) discloses a process wherein tetrafluoroethylene is reacted with another fluorinated ethylene in the liquid phase to produce a polyfluoroolefin product.

Notwithstanding the above-noted process and other processes for producing fluorinated olefins in general and fluorinated propenes in particular, applicants have come to appreciate that a need remains for a more economically efficient means of producing hydrofluoroolefins in general and hydrofluoropropenes in particular, such as HFO-1234yf. The present invention satisfies this need among others.

SUMMARY

The present invention relates, in part, to one or more process steps for improving the reaction efficiency used for the production of HFOs, such as 2,3,3,3-tetrafluoropropene (1234yf).

In one aspect, the present invention relates to a process for preparing 2-chloro-3,3,3-trifluoropropene by providing a starting composition including at least one compound of formula I, II, and/or III

$$CX_2 = CCl - CH_2X \qquad (I)$$

$$CX_3 - CCl = CH_2 \qquad (II)$$

$$CX_3 - CHCl - CH_2X \qquad (III)$$

wherein X is independently selected from F, Cl, Br, and I, provided that at least one X is not fluorine. Such starting composition is contacted with a fluorinating agent to produce a final composition including 2-chloro-3,3,3-trifluoropropene (1233xf), HCl, unreacted HF, optional unreacted starting compound(s), and one or more by-products. The by-products may include one or a combination of trichlorofluoropropene (1231) isomers, 2,3-dichloro-3,3-difluoropropene (1232xf), 2-chloro-1,1,1,2-tetrafluoropropane (244bb), 1,1,1,2,2-pentafluoropropane (245cb), dichlorotrifluoropropane (243), trichlorodifluoropropane (242), and dimer(s) such as $C_6H_3F_6Cl$, $C_6H_3F_7Cl_2$, $C_6F_6Cl_2$, $C_6H_8Cl_2$, $C_6F_5Cl_3$, and/or $C_6H_3F_2Cl_5$. In certain aspects, at least one of the compounds is recyclable to the contacting step.

This final composition is then processed to separate desired products and recyclables from the remainder of the composition. In one aspect, 1233xf and HCl are first separated by feeding the composition into a recycle or distillation column. From such a column, the lighter components, such as 1233xf, 244bb (if any), 245cb (if any), HCl, and a portion of unreacted HF are isolated in a first or top stream, and the remaining components, such as unreacted HF, optional unreacted starting compounds, one or more by-products, and residual 1233xf are recovered in a second or bottom stream. From the top stream, 1233xf is purified using standard distillation methods, such as those provided herein. It is then forwarded to the second step of the reaction (discussed below) to produce 244bb and, ultimately, 1234yf.

The bottom stream of the recycle or distillation column is then further processed to isolate recyclable compounds from the first reaction step. Unreacted HF, for example, is substantially separated by phase separation. More specifically, the second or bottom stream from the recycle column is provided to a phase separator where unreacted HF separates into a first layer. In certain embodiments, this first layer also includes, as a residual portion, certain of the organics such as, but not limited to, 1233xf, 1232xf, and 243. The remaining organics (e.g. optional unreacted starting compound, residual 1233xf, and one or more by-products, which may include 1232xf and/or 243) are separated into a second layer. The HF-rich first layer is then extracted, optionally purified, and recycled. The second layer may be similarly extracted and the unreacted starting material (if any) and recyclable products and/or by-products purified for recycling.

In an alternative embodiment of the foregoing, the final composition of the reaction includes each of at least 2-chloro-3,3,3-trifluoropropene (1233xf), HCl, unreacted HF, optional unreacted starting compound, trichlorofluoropropene (1231)

isomers, 2,3-dichloro-3,3-difluoropropene (1232xf), a first by-product selected from the group consisting of 1,1,1,2-tetrafluoropropane (244bb), 1,1,1,2,2-pentafluoropropane (245cb), and combinations thereof, a second by-product selected from the group consisting of dichlorotrifluoropropane (243), trichlorodifluoropropane (242), and combinations thereof, and a third by-product selected from the group consisting of $C_6H_3F_6Cl$, $C_6H_3F_7Cl_2$, $C_6F_6Cl_2$, $C_6H_8Cl_2$, $C_6F_5Cl_3$, $C_6H_3F_2Cl_5$, and combinations thereof.

The final composition is then fed into a recycle or distillation column, where the lighter components, such as 1233xf, first by-product(s), HCl, and a portion of unreacted HF are isolated from the column in a first or top stream. The remaining components, such as unreacted HF, optional unreacted starting compounds, residual 1233xf, trichlorofluoropropene (1231) isomers, 2,3-dichloro-3,3-difluoropropene (1232xf), second by-product(s) and third by-product(s) are recovered in a second or bottom stream.

From the top stream, the 1233xf is purified using standard methods, such as those described herein, and forwarded to the second stage of the reaction to produce 244bb.

The compounds in the bottom stream may then be further separated to isolate recyclable compounds from the first reaction step. Unreacted HF, for example, is separated by phase separation. More specifically, the second stream from the recycle column is provided to a phase separator where the majority of unreacted HF separates into a first layer. In certain embodiments, this first layer also includes, as a residual portion, certain of the organics such as, but not limited to, 1233xf, 1232xf, and 243. The remaining organics not provided in the first layer (e.g. optional unreacted starting compound, residual amounts of 1233xf, 1231 isomers, 1232xf, and second and third by-product(s)), and a small portion of unreacted HF) are separated into a second layer. The first layer, which is rich in HF, is then extracted, optionally purified, and recycled. With the second layer, the optional unreacted starting compound, trichlorofluoropropene (1231) isomers, 2,3-dichloro-3,3-difluoropropene (1232xf), second by-product(s) are separated from the third by-products by a high boiler purge system. The optional unreacted starting compound, trichlorofluoropropene (1231) isomers, 2,3-dichloro-3,3-difluoropropene (1232xf), residual amounts of 1233xf and second by-product(s) may then be recycled to the reactor.

Applicants have discovered that the separation of the components in the bottom stream of the first recycle column (e.g. HF, unreacted starting compound, and certain by-products) allows for easier recycle of reactants back into reactor. The economy of the process is also improved by purifying such recycles and removing undesirable by-products that deleteriously affect catalyst life or otherwise degrade the reactor. To this end, the processes of the present invention result in reduced catalyst deactivation, as a result of the recycles, and corrosion of the reactor is minimized. Additional embodiments and advantages to the present invention will be readily apparent to one of skill in the art, based on the disclosure provided herein.

DETAILED DESCRIPTION OF THE INVENTION

Figure 1:
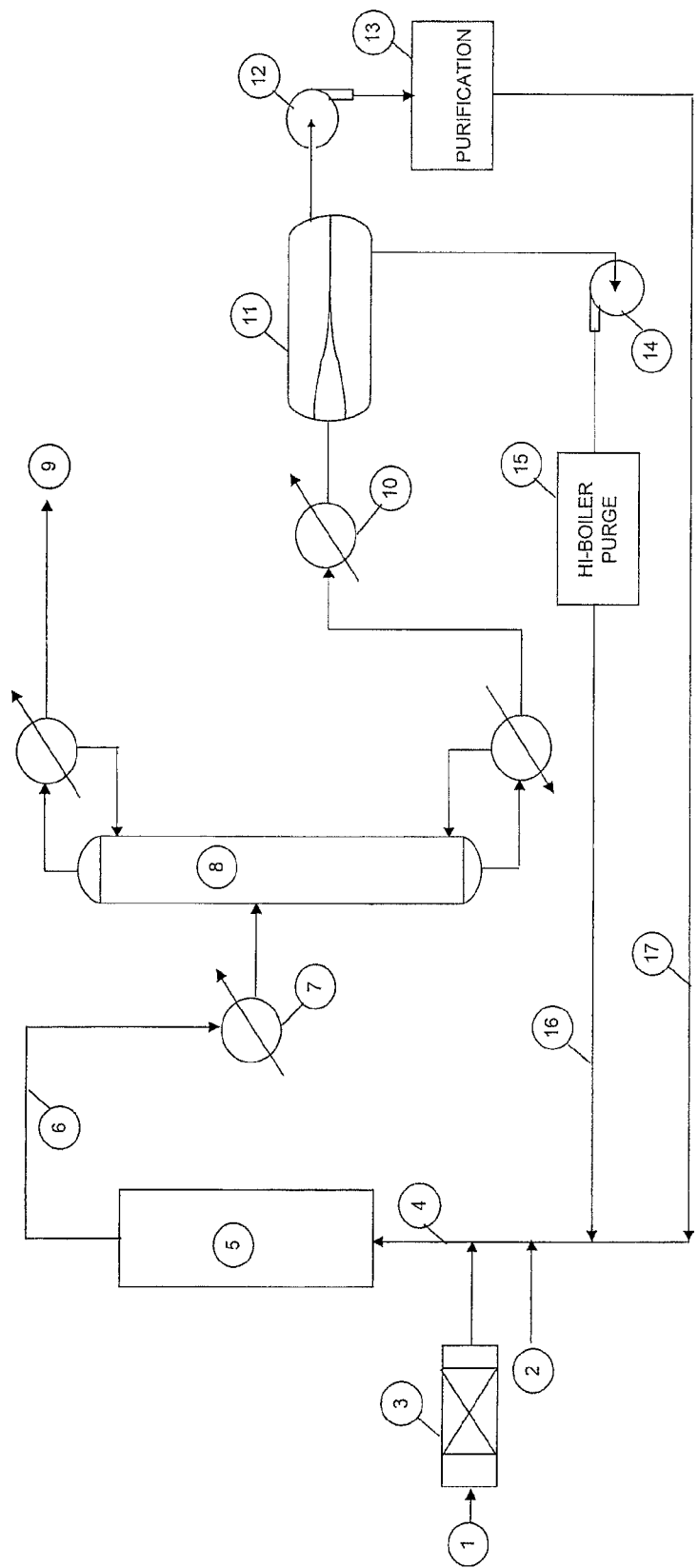
FIG. 1 provides a schematic overview of one embodiment of the process of removing 1233xf and recyclable compounds from the 1233xf product stream.

According to one embodiment, the present invention relates to a manufacturing process for making 2,3,3,3-tetrafluoroprop-1-ene using a starting material according to any one or combination of formulas I, II, and/or III:

$CX_2=CCl-CH_2X$   (Formula I)

$CX_3-CCl=CH_2$   (Formula II)

$CX_3-CHCl-CH_2X$   (Formula III)

wherein X is independently selected from F, Cl, Br, and I, provided that at least one X is not fluorine. In certain embodiments, the compound(s) of Formula I, II and/or III contains at least one chlorine, a majority of the Xs as chlorine, or all Xs as chlorine. In certain embodiments, the compound(s) of formula I includes 1,1,2,3-tetrachloropropene (1230xa). In certain embodiments, the compound(s) of formula II includes 2,3,3,3-tetrachloropropene (1230xf). In further embodiments, the compound(s) of formula III include 1,1,1,2,3-pentachloropropane (240db).

The method generally includes at least three reaction steps. In the first step, a starting composition including compounds of Formula I, II, and/or III (e.g. 1,1,2,3-tetrachloropropene, 2,3,3,3-tetrachloropropene, and/or 1,1,1,2,3-pentachloropropane) is reacted with anhydrous HF in a first vapor phase reactor (fluorination reactor) to produce a mixture of 2-chloro-3,3,3-trifluoropropene (1233xf) and HCl. In certain embodiments, the reaction occurs in the vapor phase in the presence of a vapor phase catalyst, such as, but not limited to, a fluorinated chromium oxide. The catalyst may (or may not) have to be activated with anhydrous hydrogen fluoride HF (hydrogen fluoride gas) before use depending on the state of the catalyst.

While fluorinated chromium oxides are disclosed as the vapor phase catalyst, the present invention is not limited to this embodiment. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures and any one of which may be optionally fluorinated.

Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

This first step of the reaction may be conducted in any reactor suitable for a vapor phase fluorination reaction. In certain embodiments, the reactor is constructed from materials which are resistant to the corrosive effects of hydrogen fluoride and catalyst such as Hastalloy, Nickel, Incoloy, Inconel, Monel and fluoropolymer linings. If desired, inert gases such as nitrogen or argon may be employed in the reactor during operation.

When the compound of formula I is 1230xa, the mol ratio of HF to 1230xa in step 1 of the reaction is 1:1 to 50:1, from about 10:1 to about 50:1, or from about 10:1 to about 20:1. The reaction between HF and 1230xa is carried out at a temperature from about 200° C. to about 600° C., in certain embodiments, about 200° C. to about 400° C., or about 200°

C. to about 300° C. The reaction pressure is about of about 0 psig to about 500 psig, in certain embodiments from about 20 psig to about 200 psig, or about 50 to about 100 psig.

Similarly, when the compound of formula II is 1230xf, the mol ratio of HF to 1230xf in step 1 of the reaction is 1:1 to 50:1, from about 10:1 to about 50:1, or from about 10:1 to about 20:1. The reaction between HF and 1230xf is carried out at a temperature from about 200° C. to about 600° C., in certain embodiments, about 200° C. to about 400° C., or about 200° C. to about 300° C. The reaction pressure is about of about 0 psig to about 500 psig, in certain embodiments from about 20 psig to about 200 psig, or about 50 to about 100 psig.

Similarly, when the compound of formula III is 240db, the mol ratio of HF to 240db in step 1 of the reaction is 1:1 to 50:1, from about 10:1 to about 50:1, or from about 10:1 to about 20:1. The reaction between HF and 240db is carried out at a temperature from about 200° C. to about 600° C., in certain embodiments, about 200° C. to about 400° C., or about 200° C. to about 300° C. The reaction pressure is about of about 0 psig to about 500 psig, in certain embodiments from about 20 psig to about 200 psig, or about 50 to about 100 psig.

The fluorination reaction may be carried out to attain a single- or multi-pass conversion of at least 1% or higher, 5% or higher, 10% or higher or about 20% or higher. In certain preferred embodiments of the present invention, the starting reagent is converted to 1233xf in a single pass, wherein the reaction conditions achieve a conversion amount greater than 75%, greater than 85%, greater than 95% or greater than 99%. To this end, the resulting effluent includes small or trace amounts of unreacted starting material or may be substantially free of such compounds.

The effluent from the fluorination reaction step, including any intermediate effluents that may be present in multi-stage reactor arrangements, are processed to achieve desired degrees of separation and/or other processing. For example, in embodiments in which the reactor effluent includes 1233xf, the effluent will generally also include HCl, unreacted HF, and trace amounts, if any, of unreacted starting component (e.g. 1230xa, 1230xf and/or 240db). The effluent may also include one or more by-product organics such as underfluorinated and/or overfluorinated intermediates. Non-limiting examples of underfluorinated intermediates include trichlorofluoropropene (1231) isomers and 2,3-dichloro-3,3-difluoropropene (1232xf), and non-limiting examples of overfluorinated intermediates include 2-chloro-1,1,1,2-tetrafluoropropane (244bb) and 1,1,1,2,2-pentafluoropropane (245cb). Other by-product organics may also include, but are not limited to, dichlorotrifluoropropane (243), and trichlorodifluoropropane (242) and dimers derived from one or more of the starting compounds. By way of non-limiting example, dimers derived from 1230xa include, but are not limited to, $C_6H_3F_6Cl$, $C_6H_3F_7Cl_2$, $C_6F_6Cl_2$, $C_6H_8Cl_2$, $C_6F_5Cl_3$, $C_6H_3F_2Cl_5$, and the like.

The effluent may be processed in one or more steps to isolate the 1233xf, as well as certain unreacted components and/or byproducts that are useful as a recyclables. In one embodiment, and referring to FIG. 1, starting reagent 1 is provided to a drier 3 and then to the reactor 5 along with HF 2. The effluent stream 6 exiting the vapor phase reactor 5 is fed to a cooler 7 and then to a first recycle column, such as a distillation column 8. The lighter components of the effluent 9 are isolated from the top of the first recycle column and cooled and include one or more of HCl, 1233xf, 244bb (if any), 245cb (if any) and a portion of unreacted HF. The remaining compounds are collected at the bottom stream of the column and include a bulk of the unreacted HF, trace amounts of unreacted starting component (if any), residual 1233xf and one or more of the by-product organics discussed herein. When referring to the bottom stream of the column, a "residual" amount of 1233xf refers to less than about 30 wt %, less than about 20%, less than about 15%, or less than about 10% of the total weight of the components in the bottom stream.

Each of the top stream and bottom stream are then independently processed. The top stream, for example, is first fed into an HCl column (not illustrated) for HCl removal. High purity HCl is isolated from the top of the column and fed to an HCl recovery system. By way of non-limiting example, in such a recovery system HCl from the top stream may be absorbed in de-ionized water as concentrated HCl which, optionally, can be recovered for later sale. The remaining components, including 1233xf, 244bb (if any), 245cb (if any), and HF, exit the bottom of the HCl column and are further processed. In certain embodiments, this bottom stream is then provided to an HF recovery system to recover HF. The 1233xf/HF stream is fed to a sulfuric acid extractor or a phase separator for removal of HF from this mixture, i.e. the HF is either dissolved in sulfuric acid or phase separated from the organic mixture. With the former, HF is desorbed from the sulfuric acid/HF mixture by heating and distillation and recycled back to the reactor. In the case where a phase separator is used, HF is phase-separated using standard methods, such as those discussed below, and recycled back to the reactor. The organic either from the overhead of the sulfuric acid extractor or from the bottom layer of the phase separator is fed to the hydrofluorination reactor of Step (2), discussed below.

Components within the bottom stream of the first recycle column 5 are separated, in certain embodiments, by phase separation. More specifically, the mixture is provided to a cooler 10 and then to a phase separator 11 where unreacted HF separates into an HF-rich first or top layer and an organic rich bottom or second layer. Any pressure which maintains the mixture substantially in the liquid phase may be employed. To this end, the pressure and temperature of the mixture may be adjusted such that the mixture remains substantially in the liquid phase. In certain embodiments, the HF-rich layer also includes, as a residual portion, certain of the organics such as, but not limited to 1233xf, 1232xf and 243. The remaining organics not provided in the first layer (particularly unreacted starting compound(s) (if any), residual 1233xf, 242 isomers, 243 isomers and dimers) separate into the organic-rich second or bottom layer. (When referring to the top layer, a "residual portion" of organics refers to less than about 50 wt %, less than about 40%, less than about 30%, less than about 20%, or less than about 10% of the total weight of the components in the top layer.) Phase separation may be performed at any combination of temperature and pressure such that two distinct liquid phases are formed in the phase separator. Phase separation may be carried out between about −30° C. to 60° C., preferably between about 0° C. and 40° C. and more preferably between about 10° C. and 30° C.

The HF rich layer is then isolated, such as by HF phase pump 12, optionally purified 13, and recycled 17 back to the reactor via vaporizer. In one embodiment, the HF-rich layer is distilled to remove any moisture buildup or is isolated by single stage flash distillation. In another embodiment, before the recycle of HF-rich stream moisture (if any) is removed by injecting a chemical reagent such as $COCl_2$ (or $SOCl_2$) into said stream, which reacts with moisture to form $CO_2$ (or $SO_2$) and HCl. In even further embodiments, the HF-rich layer may be purified to remove the residual organics or may be recycled with the organics.

Figure 2:
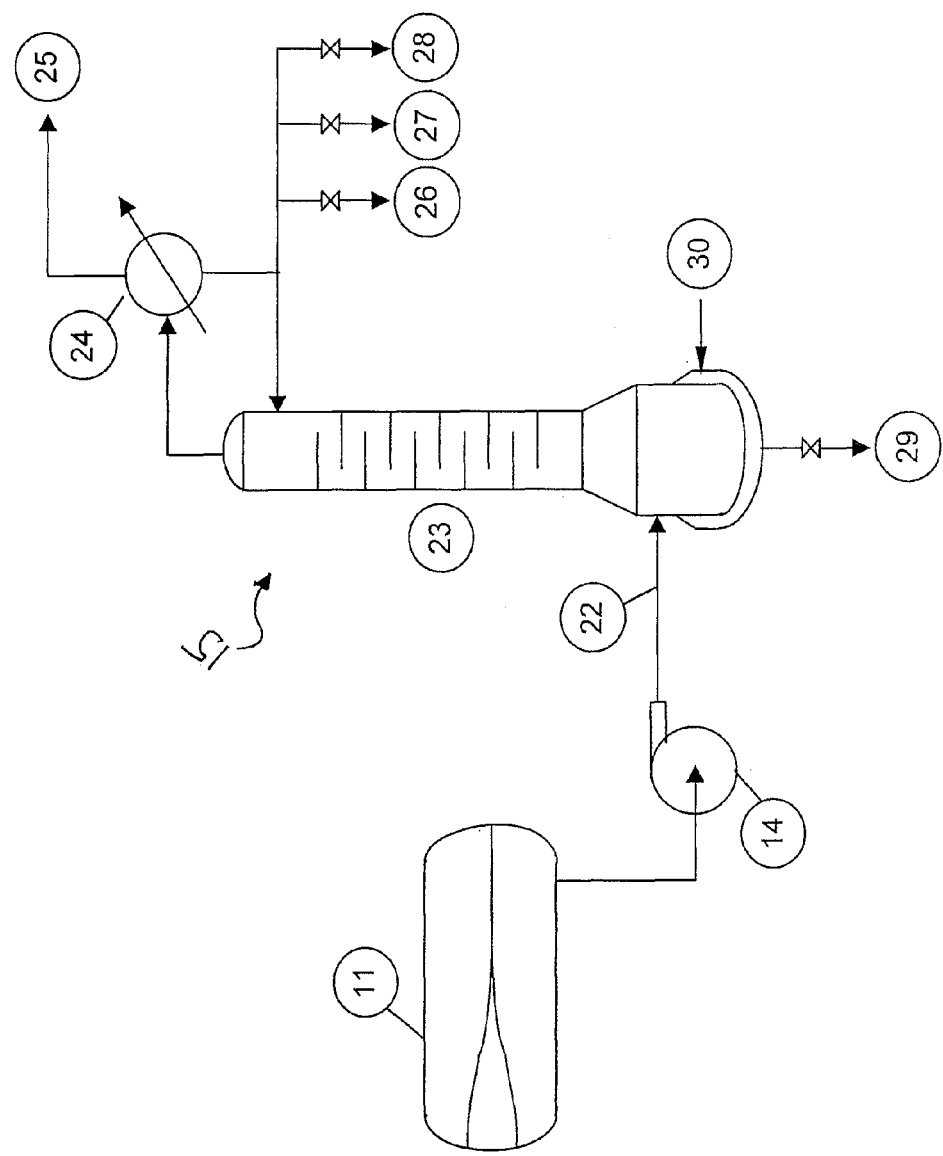
FIG. 2 provides a schematic overview of the high boiler purge system.

The organic-rich layer is also isolated, such as by organic phase pump 14, then further processed to separate and purify the unreacted starting reactants (if any) and recyclable intermediates. In certain embodiments, the organic-rich layer is provided to a high boiler purge system 15, where unreacted starting reagents (if any), residual 1233xf, 1231 isomers, 1232xf, 243 isomers, 242 isomers, etc. are recovered and undesirable by-products, particularly dimers and other impurities, are removed. (When referring to the organic-rich layer, a "residual" amount of HF refers to less than about 15 wt %, less than about 10%, less than about 5%, or less that about 3% of the total weight of the components in the bottom layer.) The high boiler purge system may be a distillation system operated in batch or continuous mode, preferably batch for operational reasons. Another option is to use a flash or series of flashes. In either case (distillation or flash), the more volatile components are recovered and recycled while the heavier components are removed from the system. In one non-limiting embodiment, and referring to FIG. 2, feed 22 from the organic phase pump 14 is provided to a batch distillation column and heated via steam supply 30. The lighter components (e.g. unreacted starting compounds including HF, 1231 isomers, 1232xf, residual 1233xf, 242 isomers, and 243 isomers) are isolated from a top stream and are cooled in condenser 24. Non-condensable compounds (if any) are optionally purged 25 and the remaining compounds are collected as a series of distillation cuts where compounds are separated in order of volatility. While FIG. 2 illustrates three distillation cuts 26, 27, 28, Applicants note that the present invention is not limited thereto and the any number of distillation cuts may be provided to separate the valuable or recyclable materials, e.g. unreacted starting compounds, 1231 isomers, 1232xf, 1233xf, 243 isomers, 242 isomers, etc. Once isolated, and referring back to FIG. 1, unreacted starting compounds, 1233xf, 1231 isomers, 1232xf, 243 isomers, 242 isomers may be recycled 16 to the reactor 5. In doing so, the unreacted starting components (if any) and the recyclable intermediates are converted to the desired composition 1233xf and/or its precursors. The heavy compounds (e g dimers, etc.) are isolated from the bottom stream 29.

Applicants have discovered that the separation of the components in the bottom stream of the first recycle column into two phases allows for easier recycle of reactants back into reactor, and that the economy of the process is improved by using phase separator followed by purification of one or both layers before recycling. A presence of moisture in the feed, for example, leads to catalyst deactivation and corrosion of equipment and piping. Such moisture, if present, will typically concentrate in the HF-rich layer during phase separation. Accordingly, by purifying the HF-rich layer post-isolation, the moisture may be removed and the catalyst deactivation and corrosion minimized.

Removal of the high boiling point by-products and impurities is similarly advantageous because such compounds also cause catalyst deactivation if recycled. During phase separation, as set forth above, such compounds tend to concentrate in organic layer. Accordingly, post-isolation, the organic layer can also be purified in accordance with the foregoing to remove such compounds and isolate only those compound that are recyclable. Removal of the high boiling point compounds results in improved catalyst life and minimal purge streams.

In the second step of the process for forming 2,3,3,3-tetrafluoroprop-1-ene, the purified 1233xf intermediate stream is converted to 2-chloro-1,1,1,2-tetrafluoropropane (244bb). In one embodiment, this step may be performed in the liquid phase in a liquid phase reactor, which may be TFE or PFA-lined. Such a process may be performed in a temperature range of about 70-120° C. and about 50-120 psig.

Any liquid phase fluorination catalyst may be used in the invention. A non-exhaustive list include Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

This second step of the reaction is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the 1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

In the third step of 1234yf production, the 244bb is fed to a second vapor phase reactor (dehydrochlorination reactor) to be dehydrochlorinated to make the desired product 2,3,3,3-tetrafluoroprop-1-ene (1234yf). This reactor contains a catalyst that can catalytically dehydrochlorinate HCFC-244bb to make HFO-1234yf.

The catalysts may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625. Such catalysts may be provided as discrete supported or unsupported elements and/or as part of the reactor and/or the reactor walls.

Preferred, but non-limiting, catalysts include activated carbon, stainless steel (e.g. SS 316), austenitic nickel-based alloys (e.g. Inconel 625), nickel, fluorinated 10% CsCl/MgO, and 10% CsCl/MgF$_2$. The reaction temperature is preferably about 300-550° C. and the reaction pressure may be between about 0-150 psig. The reactor effluent may be fed to a caustic scrubber or to a distillation column to remove the by-product of HCl to produce an acid-free organic product which, optionally, may undergo further purification using one or any combination of purification techniques that are known in the art.

The following are examples of the invention and are not to be construed as limiting.

EXAMPLES

Example 1

The pilot demonstration unit is composed of feed delivery system, vaporizer, reactor/heating system, distillation column, phase separator, recycle system, caustic solution scrubber, and product (1233xf) collection system. During start-up, organic feed containing 10 weight % 1233xf and 90 weight % 1230xa was passed through a drying column and combined with HF feed before entering vaporizer. The vaporized vapor mixture was then introduced into reactor, which was charged with 6.5 L of fluorinated chromium oxide catalyst. The reaction temperature and pressure were 200° C. and 70 psig, respectively. The reactor effluent was directed to a cooler operated at −30° C. before entering a distillation column operated at 60 psig. The effluent from the top of the distillation column (1233xf, HCl, and HF, and 244bb/245cb (if any)) was passed through a scrubber, drying column and then to a Product Collection Cylinder (PCC). The effluent from the bottom of the distillation column (mainly HF, unreacted 1230xa (if any), 1232xf and other underfluorinated compounds and various by-products) are sent through a heat exchanger (cooler) and then to a phase separator (PS), which is a 20-gallon vessel equipped with a pressure transducer, thermocouple, sight tube, rupture disk, and dip tube, and was operated at about 25° C. and about 25 psig in this example. The length of the dip tube is 50% of the length of the PS. HF recycle was initiated once enough material was accumulated in the PS. Samples were periodically taken from the top and bottom of PS and were analyzed. As shown in Table 1, the top layer was HF rich while the bottom one was organic rich. As shown in Table 2, the organics in HF-rich layer were mainly composed of lighter components, such as 1233xf, 1232xf, etc., while those in organic-rich layer those lighter components were less than 50%. These results indicate that a phase separator allows one to remove heavy components from HF-rich layer.

TABLE 1

| Phase | Composition, wt % | |
|---|---|---|
| | HF | Organic |
| Top layer (HF-rich) | 63.5 | 36.5 |
| Bottom layer (Organic-rich) | 3.1 | 96.9 |

TABLE 2

| Phase | Organic composition, GC area % | | | |
|---|---|---|---|---|
| | 1233xf | 243 | 1232xf | others |
| Top layer (HF-rich) | 82.11 | 2.84 | 13.62 | 1.43 |
| Bottom layer (Organic-rich) | 10.28 | 4.74 | 27.71 | 57.27 |

Example 2

The same pilot demonstration unit was used as in Example 1. HF recycle was initiated by pumping the liquid of HF-rich layer through the dip tube of phase separator. The analysis of reactor effluent showed no 1230xa was detected after 1000 hours on stream, indicating no deactivation occurred during this period of time.

Comparative Example 2

The same pilot demonstration unit is used as in Example 1. Besides the HF recycle stream, organic recycle is also initiated by pumping the liquid of organic-rich layer through the bottom of phase separator. The analysis of reactor effluent shows significant amount of 1230xa is detected after 100 h on stream, indicating deactivation occurs during this period of time.

What is claimed is:

1. A process for preparing 2-chloro-3,3,3-trifluoropropene comprising:
   providing a composition comprising at least one starting compound of formula I, II and/or formula III $$CX_2=CCl-CH_2X \qquad (I)$$

$$CX_3-CCl=CH_2 \qquad (II)$$

$$CX_3-CHCl-CH_2X \qquad (III)$$

wherein X is independently selected from F, Cl, Br, and I, provided that at least one X is not fluorine;
   (a) contacting said starting composition with a fluorinating agent to produce a final composition comprising 2-chloro-3,3,3-trifluoropropene, HCl, unreacted HF, optional unreacted starting compound, and one or more by-products selected from the group consisting of trichlorofluoropropene (1231) isomers, 2,3-dichloro-3,3-difluoropropene (1232xf), 2-chloro-1,1,1,2-tetrafluoropropane (244bb), 1,1,1,2,2-pentafluoropropane (245cb), dichlorotrifluoropropane (243), trichlorodifluorpropane (242), $C_6H_3F_6Cl$, $C_6H_3F_7Cl_2$, $C_6F_6Cl_2$, $C_6H_8Cl_2$, $C_6F_5Cl_3$, $C_6H_3F_2Cl_5$, and combinations thereof, wherein at least one by-product is recyclable to the contacting step;
   (b) separating the final composition into a first stream comprising 2-chloro-3,3,3-trifluoropropene and HCl and a second stream comprising the optional unreacted starting compound, the one or more by-products, and unreacted HF;
   (c) separating the 2-chloro-3,3,3-trifluoropropene of the first stream from the HCl;
   (d) separating the unreacted HF of the second stream from the optional unreacted starting compound and one or more by-products; and
   (e) separating and recycling recyclable by-product(s) to contacting step (a).

2. The process of claim 1, wherein the separating step (b) comprises distillation wherein at least the 2-chloro-3,3,3-trifluoropropene and HCl is recovered in a first stream and at least the optional unreacted starting compound, one or more by-products, and a portion of the unreacted HF are recovered in a second stream.

3. The process of claim 1, wherein the 2-chloro-3,3,3-trifluoropropene of the first stream is separated from the HCl in step (c) by distillation.

4. The process of claim 1, wherein in step (d) the unreacted HF is separated from the optional unreacted starting compound and one or more by-products by phase separation, wherein a first layer comprises unreacted HF and a second layer comprises the optional unreacted starting compound and one or more by-products.

5. The process of claim 4, wherein the first layer is extracted and optionally purified.

6. The process of claim 5, wherein the moisture present in the first layer is removed.

7. The process of claim 6, wherein the first layer is recycled.

8. The process of claim 4, wherein the second layer is extracted.

9. The process of claim 8, wherein the optional unreacted starting compound is isolated.

10. The process of claim 8, wherein the optional unreacted starting compound is recycled.

11. The process of claim 8, wherein the recyclable by-product is isolated.

12. The process of claim 8, wherein the recyclable by-product is recycled.

13. A process for preparing 2-chloro-3,3,3-trifluoropropene comprising:
providing a composition comprising at least one starting compound of formula I, II and/or formula III $$CX_2\!=\!CCl\!-\!CH_2X \qquad (I)$$

$$CX_3\!-\!CCl\!=\!CH_2 \qquad (II)$$

$$CX_3\!-\!CHCl\!-\!CH_2X \qquad (III)$$

wherein X is independently selected from F, Cl, Br, and I, provided that at least one X is not fluorine;
(a) contacting said starting composition with a fluorinating agent to produce a final composition comprising 2-chloro-3,3,3-trifluoropropene, HCl, unreacted HF, optional unreacted starting compound, trichlorofluoropropene (1231) isomers, 2,3-dichloro-3,3-difluoropene (1232xf), at least one first by-product selected from the group consisting of 1,1,1,2-tetrafluoropropane (244bb), 1,1,1,2,2-pentafluoropropane (245cb), and combinations thereof, at least one second by-product selected from the group consisting of dichlorotrifluoropropane (243), trichlorodifluoropropane (242) and combinations thereof, and a least one third by-product selected from the group consisting of $C_6H_3F_6Cl$, $C_6H_3F_7Cl_2$, $C_6F_6Cl_2$, $C_6H_8Cl_2$, $C_6F_5Cl_3$, $C_6H_3F_2Cl_5$, and combinations thereof;
(b) separating a first stream comprising at least the 2-chloro-3,3,3-trifluoropropene, first by-product(s), and HCl, from a second stream comprising a portion of the unreacted HF and the remainder of the final composition;
(c) separating the 2-chloro-3,3,3-trifluoropropene of the first stream from the HCl and first by-product(s); and
(d) separating the unreacted HF of the second stream from the optional unreacted starting compound, trichlorofluoropropene (1231) isomers, 2,3-dichloro-3,3-difluoropropene (1232xf), the second by-product(s), and the third by-product(s); and
(e) separating the optional unreacted starting compound, trichlorofluoropropene (1231) isomers, 2,3-dichloro-3,3-difluoropropene (1232xf), and second by-product(s) from the third by-product(s).

14. The process of claim 13, wherein the separating step (b) comprises distillation wherein at least the 2-chloro-3,3,3-trifluoropropene, first by product(s), and HCl is recovered in a first stream and at least the optional unreacted starting compound, second by-products, third by-products, and a portion of the unreacted HF are recovered in a second stream.

15. The process of claim 13, wherein the 2-chloro-3,3,3-trifluoropropene of the first stream is separated from the HCl and the first by product(s) in step (c) by distillation.

16. The process of claim 13, wherein in step (d) the unreacted HF of the second stream is separated from the optional unreacted starting compound, trichlorofluoropropene (1231) isomers, 2,3-dichloro-3,3-difluoropropene (1232xf), second by-products(s), and third by-products by phase separation, wherein a first layer comprises unreacted HF and a second layer comprises the unreacted starting compound, trichlorofluoropropene (1231) isomers, 2,3-dichloro-3,3-difluoropene (1232xf), second by-products(s), and third by-products.

17. The process of claim 16, wherein the first layer is extracted and purified.

18. The process of claim 17, wherein the moisture present in the first layer is removed.

19. The process of claim 17, wherein the first layer is recycled.

20. The process of claim 15, wherein the second layer is extracted.

21. The process of claim 16, wherein at least the optional unreacted starting compound, trichlorofluoropropene (1231) isomers, 2,3-dichloro-3,3-difluoropropene (1232xf), and second by-product separated in step (e) are recycled.

22. A separation process comprising:
a) providing a composition to a phase separator, said composition comprising
i) 2-chloro-3,3,3-trifluoropropene (1233xf),
ii) HF,
iii) one or more organics selected from the group consisting of trichlorofluoropropene (1231) isomers, 2,3-dichloro-3,3-difluoropropene (1232xf), 2-chloro-1,1,1,2-tetrafluoropropane (244bb), 1,1,1,2,2-pentafluoropropane (245cb), dichlorotrifluoropropane (243), trichlorodifluorpropane (242), and
iv) one or more dimers selected from the group consisting of $C_6H_3F_6Cl$, $C_6H_3F_7Cl_2$, $C_6F_6Cl_2$, $C_6H_8Cl_2$, $C_6F_5Cl_3$, $C_6H_3F_2Cl_5$;
b) separating the composition into a top layer and a bottom layer in said phase separator, said top layer being comprised of substantially all of the HF and 1233xf from said composition, and said second layer being comprised of substantially all of the organics and the dimers of the composition.

23. The separation process of claim 22 further comprising providing the bottom layer to a purge system wherein said dimers are substantially separated from said organics.

24. The separation process of claim 23 further comprising recycling said organics to a reactor for producing 2-chloro-3,3,3-trifluoropropene (1233xf).

25. A process for preparing 2-chloro-3,3,3-trifluoropropene (1233xf) comprising:
a) providing a composition to a phase separator, said composition comprising 2-chloro-3,3,3-trifluoropropene (1233xf), HF, one or more organics selected from the group consisting of trichlorofluoropropene (1231) isomers, 2,3-dichloro-3,3-difluoropropene (1232xf), 2-chloro-1,1,1,2-tetrafluoropropane (244bb), 1,1,1,2,2-pentafluoropropane (245cb), dichlorotrifluoropropane (243), trichlorodifluorpropane (242), and one or more dimers selected from the group $C_6H_3F_6Cl$, $C_6H_3F_7Cl_2$, $C_6F_6Cl_2$, $C_6H_8Cl_2$, $C_6F_5Cl_3$, $C_6H_3F_2Cl_5$, wherein said composition is obtained from a reactor system comprising a reactor and a recycle column;

b) separating said first composition in said phase separator into a top layer and a bottom layer in said phase separator, said top layer being comprised of substantially all of the HF and 1233xf from said composition, and said second layer being comprised of substantially all of the organics and the dimers of the composition;

c) providing said bottom layer to a purge system wherein said dimers are substantially separated from said organics; and d) recycling the organics obtained from said purge system back to the reactor.

\* \* \* \* \*